(12) United States Patent
Wu

(10) Patent No.: US 6,392,549 B1
(45) Date of Patent: May 21, 2002

(54) PORTABLE MOSQUITO REPELLING/KILLING DEVICE

(76) Inventor: Chih Hsien Wu, 5F-3, No. 123, Lane 235, Pao-Chiao Rd., Hsin Tien City, Taipei Hsien (TW)

( * ) Notice: Subject to any disclaimer, the term of this patent is extended or adjusted under 35 U.S.C. 154(b) by 0 days.

(21) Appl. No.: 09/885,910

(22) Filed: Jun. 22, 2001

(51) Int. Cl.[7] ............................................... G08B 23/00
(52) U.S. Cl. ................................ 340/573.2; 340/693.5; 340/384.2; 43/129; 43/132.1; 367/139; 422/125
(58) Field of Search .......................... 340/573.2, 384.2, 340/693.5; 43/129, 132.1; 367/139; 422/125

(56) References Cited

U.S. PATENT DOCUMENTS 6,097,300 A * 8/2000 Wei .......................... 340/573.2
6,293,044 B1 * 9/2001 Feng ........................ 340/384.2

\* cited by examiner

*Primary Examiner*—Daniel J. Wu
(74) *Attorney, Agent, or Firm*—Dougherty & Troxell

(57) ABSTRACT

A portable mosquito repelling/killing device, it has a box convenient for carrying; a power source provided by dry batteries or provided by inserting the plug seat on the box in an A.C. current socket. The box of the device is combined with a clamping member in order that the device can be hung on a person. The box is provided thereon with an elastic pusher sheet, a insertion slot, several gas emitting holes, a switch, an LED light emitting hole and an electric power spigot for connecting outwardly; and is provided therein with an oscillating circuit, a buzzer, an electric heater, a heater fixing seat and batteries supplying electric power. By emitting sound waves simulating the sounds of male mosquitoes from the buzzer driven by the oscillating circuit to repel female mosquitoes in pregnancy, or by emitting heat energy from the electric heater to make a slice of incense emit gas for killing mosquitoes, the effect of protecting persons from biting of mosquitoes and the effect of mosquito repelling/killing can thus be achieved.

6 Claims, 6 Drawing Sheets

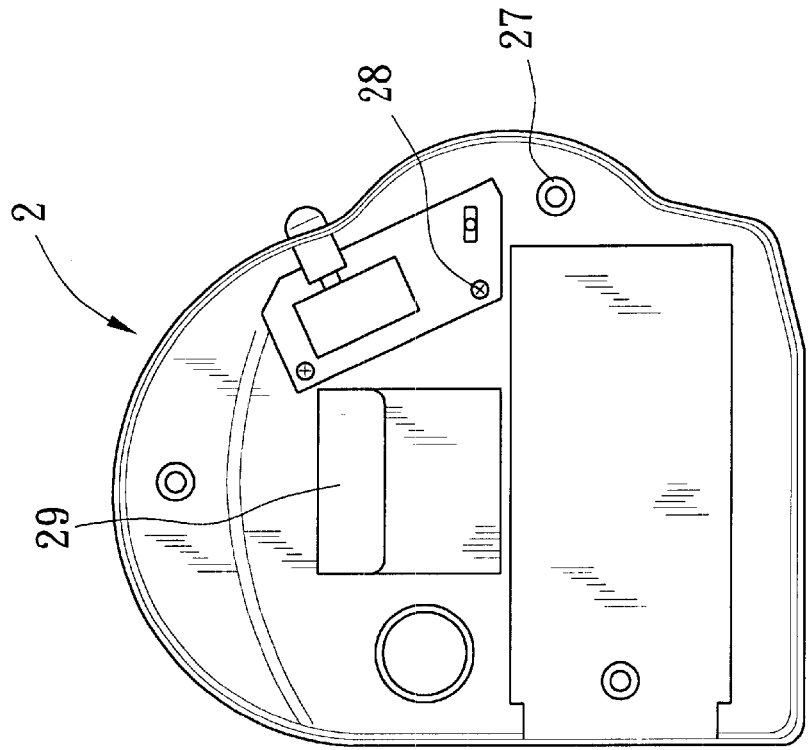
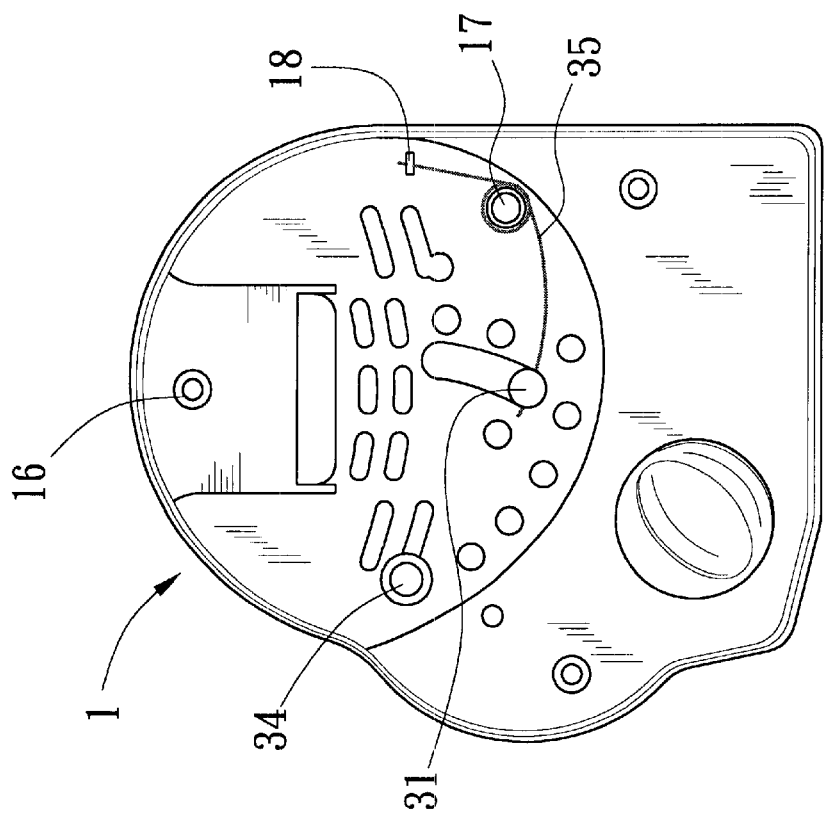

PORTABLE MOSQUITO REPELLING/KILLING DEVICE

BACKGROUND OF THE INVENTION

1. Field of the Invention

The present invention is related to a portable mosquito repelling/killing device, and especially to a box structure provided therein a buzzer and an electric heater to emit sound waves simulating the sounds of male mosquitoes or to generate heat energy that can make a mosquito-repellent slice of incense emit gas for killing mosquitoes. The present invention thereby has a mosquito repelling/killing effect, and it is light and portable, suits various fields outdoors; it is provided with an electric plug seat for inserting in an A.C. current socket when it is used in a house, i.e., it is also usable in a house.

2. Description of the Prior Art

Human has been being suffered threatening of mosquitoes since the latter existed in the world; when a mosquito bites, the skin of the man bitten irritates, not only this, he feels awful itching, and mosquitoes are the media of propagation of various diseases such as Dengue fever, malaria and Japanese encephalitis. Therefore, it is really important to be sure how to avoid mosquito bites.

However, in the most conventional mosquito repelling/killing measures such as mosquito-repellent incense, insecticide or mosquito-repellent liquid, mosquito-repellent incense is the one used by flaming of the incense to emit gas for killing mosquitoes, so that mosquitoes cannot get close to it; however, such mode of mosquito killing generates dense smoke and irritating smell which contaminates air and discomforts people, and flaming of the incense is subjected to fire disaster, this means it has latent high danger and thus is not desired.

Killing mosquitoes by using insecticide does not need burning, but it is still seriously harmful to human bodies after long-period using by virtue that the chemical medicine therein has residues not so easy to be decomposed, and this can result a problem against environmental protection; besides, using insecticide can also generate irritating smell and thus is not desired too.

Another way for mosquito repelling is spraying of mosquito-repellent liquid, the liquid is sprayed onto the skin of a person to give odor which mosquitoes are afraid of and do not dare to bite. However, such way is subjected to irritate skin and is unsuitable for long time protection especially for the whole body of a person, and it renders skin sticky. In these views, spraying of mosquito-repellent liquid is neither the best way of mosquito repelling.

In order to improve the mosquito-repellent incense, insecticide and mosquito-repellent liquid, electrically used mosquito-repellent incense and mosquito-repellent devices were provided. Electrically used mosquito-repellent incense has an electric heater to heat a mosquito-repellent slice of incense to emit gas which mosquitoes are afraid of. While a mosquito-repellent device applies the nature of mosquitoes, by the fact that biting mosquitoes all are those female mosquitoes in spawning, they do all they can to evade male mosquitoes by nature; thereby, the mosquito-repellent device emits sound waves simulating the sounds of male mosquitoes to get rid of female mosquitoes. The aforesaid two ways can both achieve the effect of mosquito repelling, they are mostly stationary and each is singly placed at a location, they can not completely meet the situations of the environment outside, and may be inefficient in mosquito repelling or may become nullified and do not meet requirement of people.

In view of this, the inventor of the present invention provided the present mosquito repelling/killing device to avoid the defects of the conventional measures; the repelling/killing device can surely be used irrespective of the environmental influence outside.

SUMMARY OF THE INVENTION

The primary object of the present invention is to provide a portable mosquito repelling/killing device to protect persons from getting closing and biting of mosquitoes.

Another object of the present invention is to provide a portable mosquito repelling/killing device which has a box combined with a clamping member in order that the device can be hung on a person; no matter how the person moves, the effect of mosquito repelling can be achieved, and the device provides convenience for carrying.

Another object of the present invention is to provide a portable mosquito repelling/killing device which can be switched freely to various modes of mosquito repelling/killing by means of an oscillating circuit or an electric heater to get the effect of preventing biting of mosquitoes, thereby, practicality as well as convenience of the device can be increased.

To achieve the above stated objects, the present invention has a box which is convenient for carrying, a power source can be provided by dry batteries or can be provided by inserting the plug seat on the box in an A.C. current socket. The box of the device is combined with a clamping member in order that the device can be hung on a person. The box is provided thereon with an elastic pusher sheet, a insertion slot, a plurality of gas emitting holes, a switch, an LED light emitting hole, an electric power spigot for connecting outwardly; and is provided therein with an oscillating circuit, a buzzer, an electric heater, a heater fixing seat and batteries supplying electric power or a plug seat for connecting outwardly. By emitting sound waves simulating the sounds of male mosquitoes from the buzzer driven by the oscillating circuit to repel female mosquitoes in pregnancy, or by emitting heat energy from the electric heater to make a mosquito-repellent slice of incense emit gas for killing mosquitoes, the effect of protecting persons from biting of mosquitoes and the effect of mosquito repelling/killing can thus be achieved.

The present invention will be apparent in its characteristics and particular structure after reading the detailed description of the preferred embodiment thereof in reference to the accompanying drawings.

BRIEF DESCRIPTION OF THE DRAWINGS

FIG. 2a is a bottom view of an upper housing of the embodiment of the present invention;

FIG. 2b is a top view of a lower housing of the embodiment of the present invention;

DETAILED DESCRIPTION OF THE PREFERRED EMBODIMENT

Figure 1:
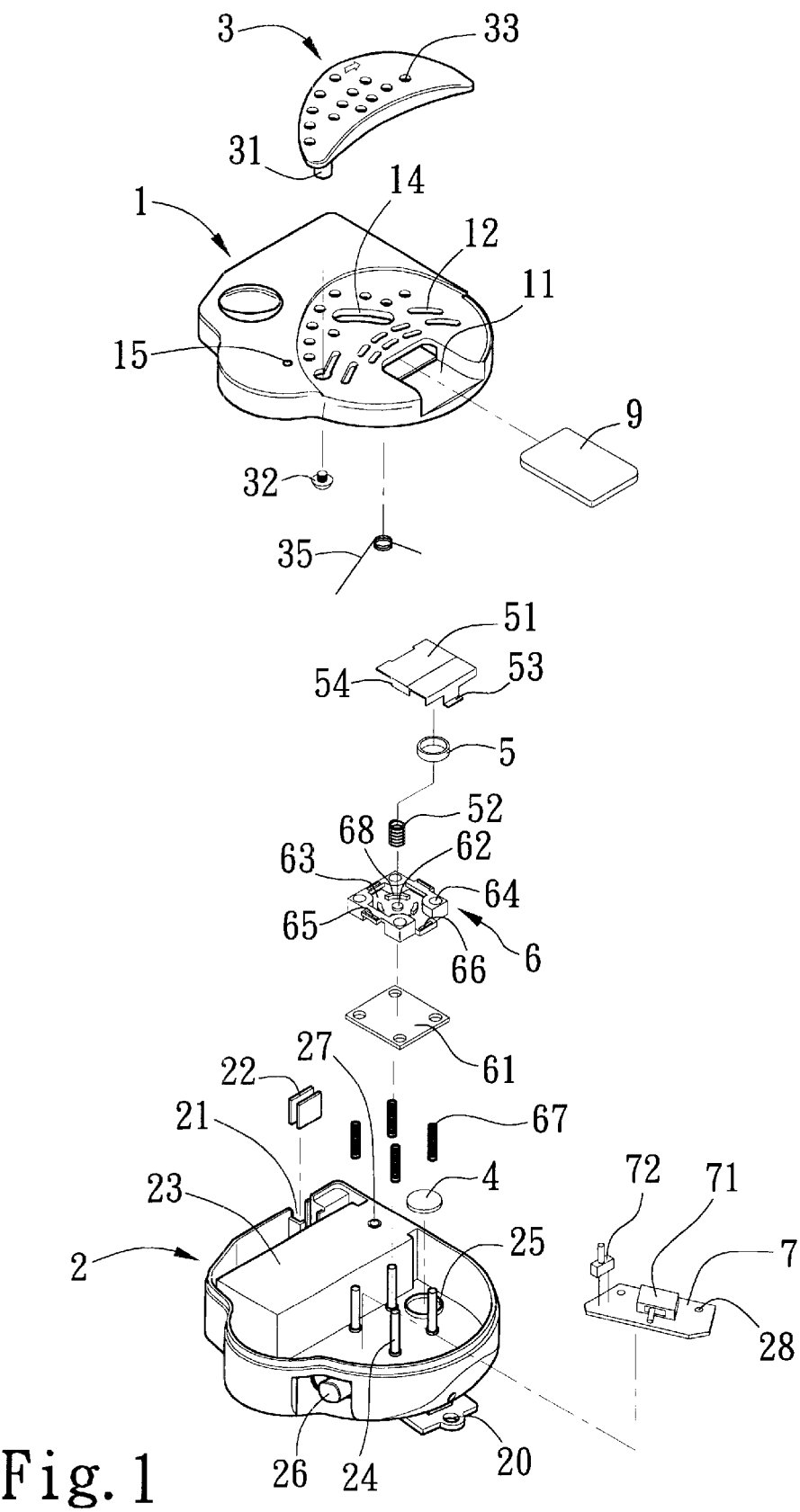
FIG. 1 is an analytical perspective view of an embodiment of the present invention.

Referring firstly to FIGS. 1 and 2, the portable mosquito repelling/killing device of the present invention has a box of suitable size, and is provided on the front side thereof with an elastic pusher sheet 3, a insertion slot 11, an LED power indicating light 72, a plurality of gas emitting holes 12; and is provided on a lateral side thereof with a switch knob 26, an electric power spigot 22 for connecting outwardly; and is provided on the back side thereof with a clamping member 20 and a battery chamber 23, also is provided therein with an oscillating circuit 7, a buzzer 4, an electric heater 5 and a heater fixing seat 6.

Wherein, as shown in FIGS. 1 and 2a, the box is composed of an upper housing 1 and a lower housing 2 connected therewith, the upper housing 1 has the rectangular recessed insertion slot 11 on the upper surface thereof for inserting a mosquito-repellent slice of incense 9 therein. The gas emitting holes 12, an arciform guide groove 14 and an LED light emitting hole 15 are provided at some suitable positions at the central area of the upper surface. The gas emitting holes 12 are covered thereon by the elastic pusher sheet 3 which is rotatable and in the shape of a half-moon. The elastic pusher sheet 3 is provided on one end thereof with a supporting post extending down into the upper housing 1, and is screw connected with the upper housing 1 with a screw 32 which can be functioned as a center of rotation of the elastic pusher sheet 3. The elastic pusher sheet 3 is provided at a suitable position in the middle area thereof with a cylindrical guide rod 34 with a hole on the top thereof; the guide rod 34 extends down into the arciform guide groove 14 in order to control sliding displacement of it in the arciform guide groove 14. The elastic pusher sheet 3 is also provided on the surface thereof with a plurality of gas emitting holes 33 in corresponding number to that of the gas emitting holes 12. The upper housing 1 is provided on the back side thereof with a plurality of threaded posts 16 to be screw connected with the lower housing 2; and is provided at a suitable position on the upper housing 1 with a protruding post 17 and an inversed "L" shaped engaging post 18. The protruding post 17 is provided thereover with a torsion spring 35 of which an end is extended into the inversed "L" shaped engaging post 18, while the other end thereof is extended into the hole on the top of the guide rod 34, the torsion spring 35 renders the elastic pusher sheet 3 able to move back automatically to its original position.

Referring to FIGS. 1 and 2b, the lower housing 2 is provided on the rear side thereof with a notch 21 for engaging the electric power spigot 22 for connecting outwardly; the lower portion of the lower housing 2 is provided with the battery chamber 23 opening downwards, both ends of the battery chamber 23 is provided therein with a plurality of polar sheets for placing batteries in. The lower housing 2 is provided at the central area thereof with a plurality of protruding posts 24, screw holes 28 and an arciform protruding ring 25, for the purpose of installation of the oscillating circuit 7, the heater fixing seat 6 and the buzzer 4. The lower housing 2 is further provided on the top thereof with an engaging hole 29 for engaging the clamping member 20; and is provided with a plurality of screw holes 27 in corresponding number to that of the threaded posts 16 for screw connecting with the upper housing 1. The lower housing 2 is further provided laterally with a switch hole having a switching knob 26 therein for moving a switch 71.

Referring also to FIGS. 1 and 2b, the oscillating circuit 7 generates signals to drive the buzzer 4 to make sound; the buzzer 4 is embedded in the arciform protruding ring 25, the oscillating circuit 7 is provided thereon the switch 71, the LED power indicating light 72 and the screw holes 28. The switch 71 is used for switching the power to the oscillating circuit 7 or the electric heater 5; the LED power indicating light 72 is used to display the state of the power source; and the screw holes 28 are used to connect the oscillating circuit 7 by screwing to the lower housing 2.

Figure 3:
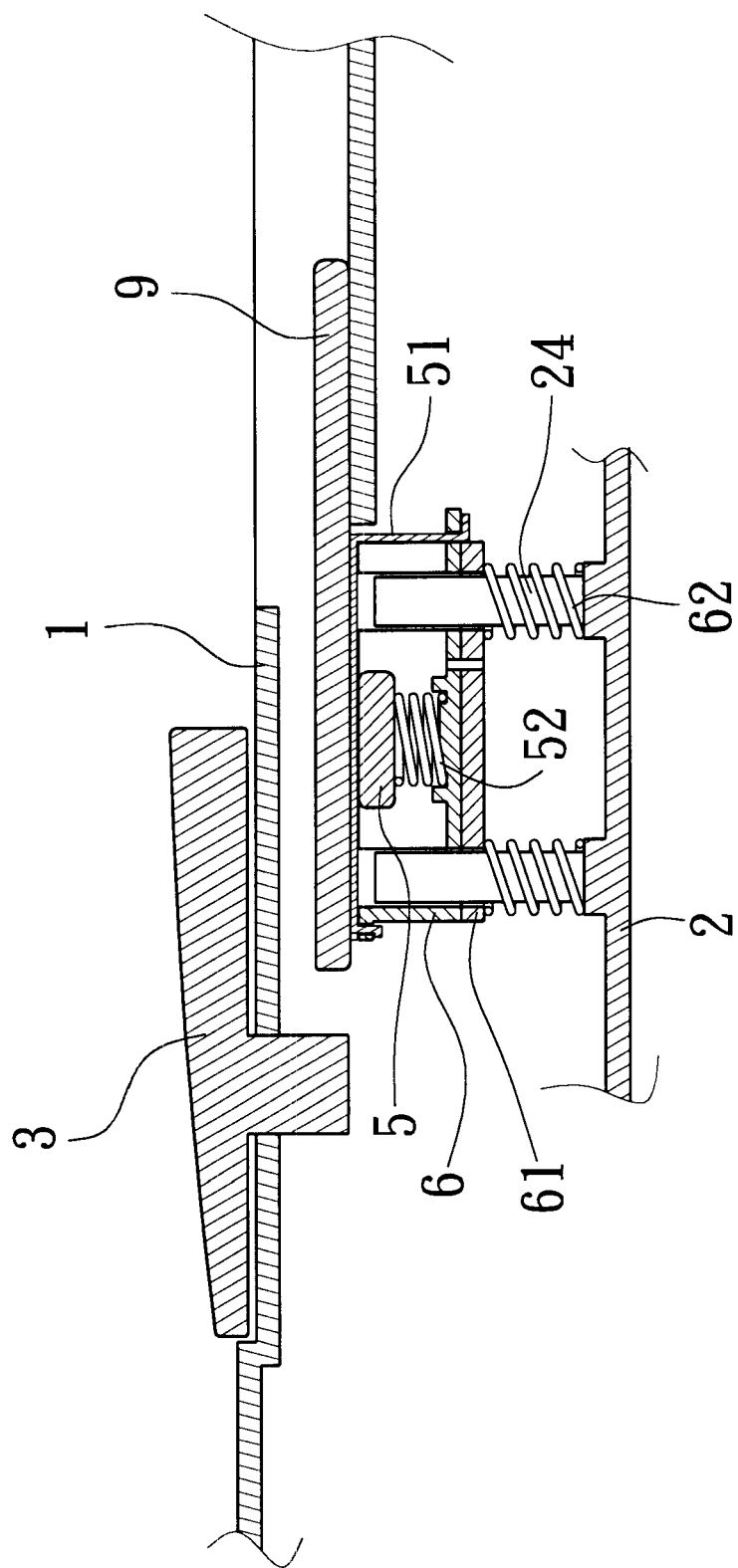
FIG. 3 is a sectional side view of the embodiment of the present invention.

Referring also to FIGS. 1 and 3, it can be seen that the heater fixing seat 6 is provided at the central area thereof with a recess 63, and is provided at the four corners thereof with blocks each having a through hole 64, a central post is provided in the recess 62 with a plurality of arciform ribs 68 thereabout. The heater fixing seat 6 is further provided on the four edges thereof each with an engaging groove 65 having an engaging hole, the engaging groove 65 on one of the edges is provided on the bottom of the heater fixing seat 6 by virtue that a notch 66 is provided thereat. Wherein, the recess 62 and the arciform ribs 68 are provided to be engaged by a spring 52, one end of the spring 52 which is an iron wire is extended through the heater fixing seat 6 to be connected to the negative pole of a battery through an electric conductor to form a negative electrode. The spring 52 is provided thereon with the electric heater 5 which is embedded in the heater fixing seat 6 by means of a copper sheet 51 of positive polarity and provided on the peripheries thereof with an engaging folding strip 54 and an insertion strip 53, the copper sheet 51 is connected to the positive pole of the battery through an electric conductor to form a heat generating circuit.

As shown in FIG. 3, a pad 61 is placed on the bottom of the heater fixing seat 6 and is mounted together with the latter onto the long protruding posts 24 having springs 67 thereon, then the oscillating circuit 7 is connected to the lower housing 2 by screwing. While the buzzer 4 is embedded in the arciform protruding ring 25, and lastly, the upper housing 1 is connected to the lower housing 2 by screwing to complete assembling of the present invention.

Figure 4B:
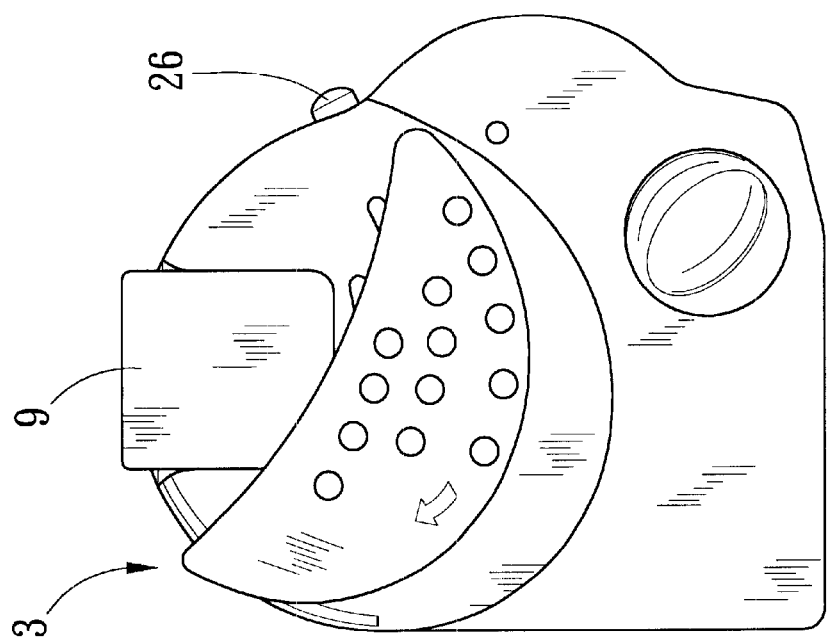
FIGS. 4a and 4b are schematic views showing use of the embodiment of the present invention.
Figure 4A:
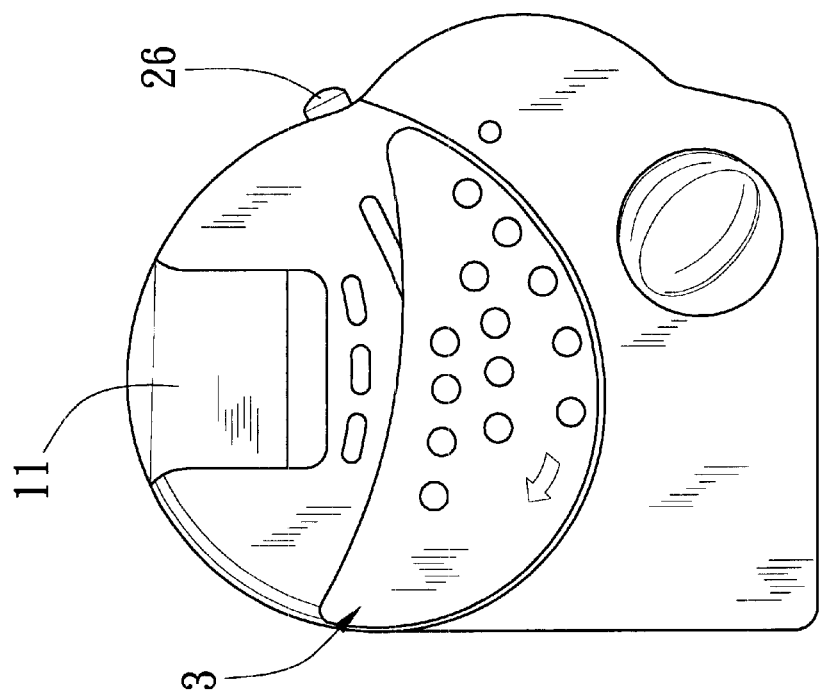

Referring also to FIGS. 4a and 4b, in using, after assembling of the portable mosquito repelling/killing device of the present invention according to the above stated sequence, when a user inserts a mosquito-repellent slice of incense 9 into the insertion slot 11, the springs 67 on the long protruding posts 24 push the heater fixing seat 6 upwardly to abut the mosquito-repellent slice of incense 9 tightly against the copper sheet 51 of positive polarity in order to avoid dropping of the slice of incense 9; the spring 52 can also abut the electric heater 5 tightly against the copper sheet 51 in order that heat emitted from the electric heater 5 can be uniformly transmitted to the copper sheet 51 with a large area to in turn render the slice of incense 9 to be heated uniformly. When the user is to change the slice of incense 9, he pushes the elastic pusher sheet 3 along the arciform guide groove 14, and then the guide rod 34 will push the slice of incense 9 out of the insertion slot 11 for removing the slice of incense 9.

Figure 5:
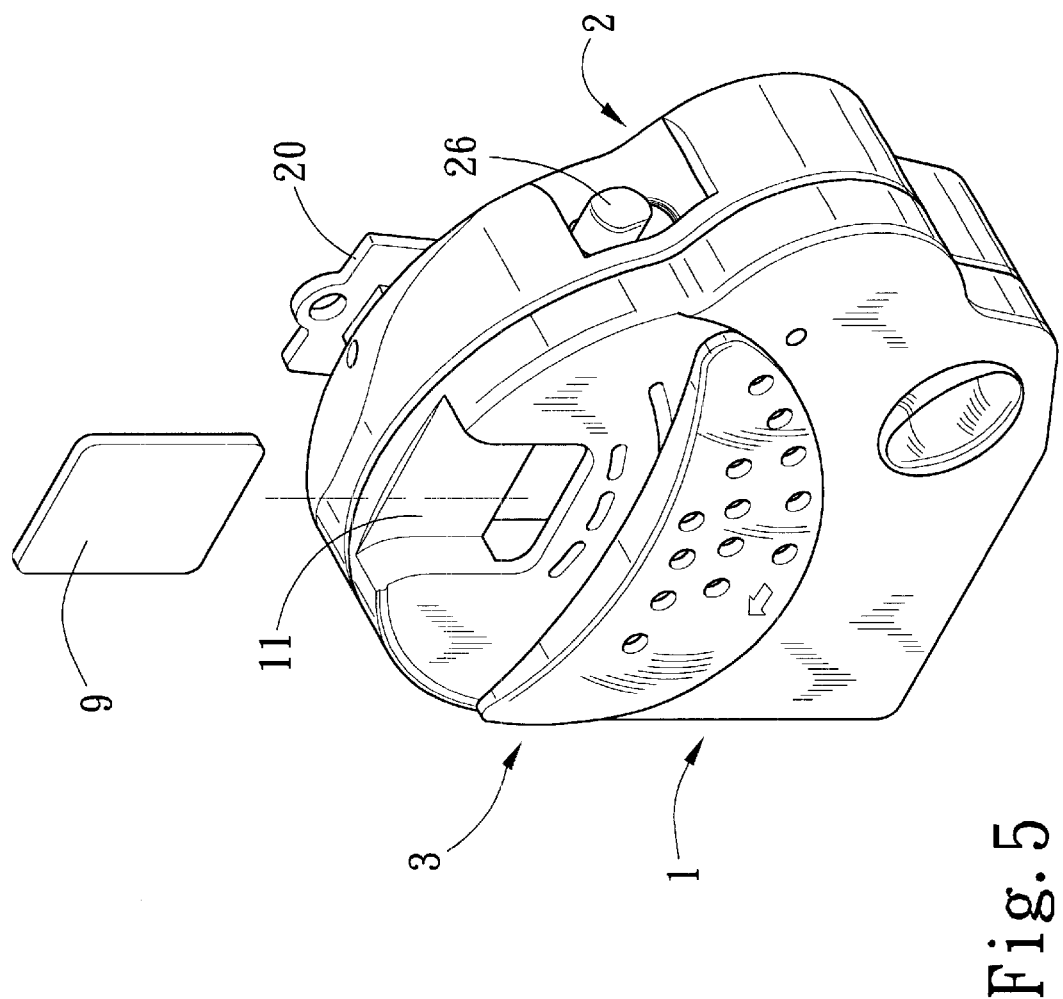
FIG. 5 is a perspective view of the embodiment of the present invention.

Referring to FIG. 5, when the present invention is used outdoors, two options can have according to the situation encountered:

1. Move the switch 71 to the first stage to turn on the oscillating circuit 7 to make the buzzer 4 generate the sound with a frequency of a male mosquito, and a mosquito-repellent effect is provided.
2. Move the switch 71 to the second stage to turn on the electric heater 5 for heating, now a mosquito-repellent slice of incense 9 is inserted into the insertion slot 11 to abut tightly against the copper sheet 51 of positive polarity. The slice of incense 9 then receives heat to emit odor which can kill mosquitoes, and a mosquito-killing effect is provided.

Figure 6:
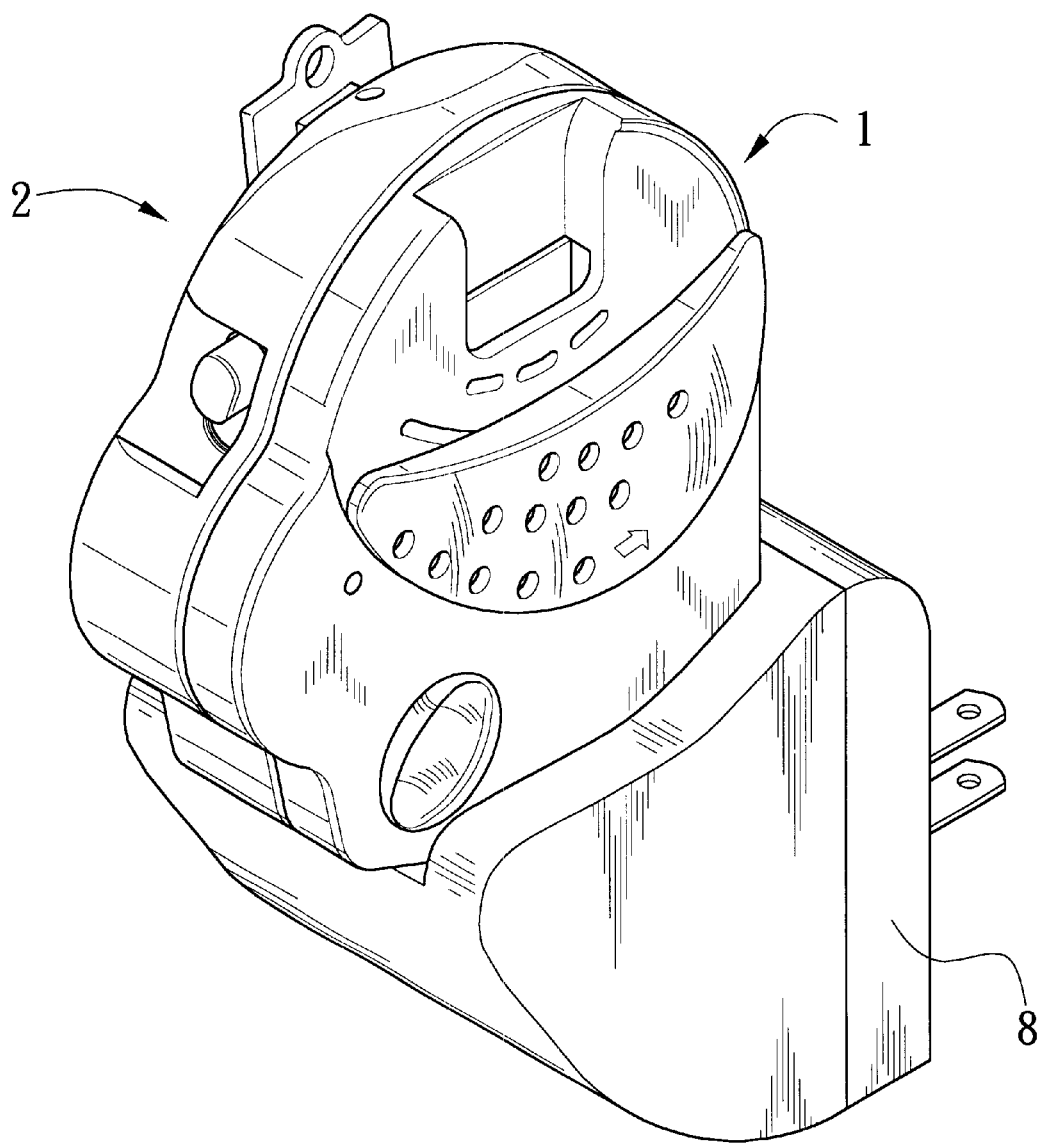
FIG. 6 is a perspective view of another embodiment of the present invention capable of connecting to an electric power outside.

Referring to FIG. 6, when the present invention is used indoors, the electric power spigot 22 for connecting outwardly can be connected with a plug seat 8 in which a transformer provides electric power, when the present invention is used in a house, it can get electric power from an A.C. power supply.

Accordingly, the present invention has the following advantages:

1. The present invention can be carried with one's person without influence of the external environment by providing the clamping member on the back side of the box of the present invention, and can get the mosquito repelling/killing effect.
2. The present invention can use a mosquito-repellent slice of incense or sound wave to repel mosquitoes, it can suit various environmental requirement.

In conclusion, the present invention can not only get rids of the defects resided in the conventional mosquito repelling/killing devices, but also can get the effect of preventing biting of mosquitoes by the heat generated by the electric heater or by the odor emitted from the mosquito-repellent slice of incense, and can thereby have the protecting effect for people in mosquito repelling/killing. The present invention can be used in various fields.

What is claimed is:

1. A portable mosquito repelling/killing device, said device has a box adapted to hanging on clothes for carrying, and is composed of an upper housing and a lower housing connected therewith by screwing, said device is characterized by:

said upper housing has a rectangular recessed insertion slot on the upper surface thereof, a plurality of gas emitting holes, an arciform guide groove and an LED light emitting hole, an elastic pusher sheet is provided on said upper housing with a protruding post and an inversed "L" shaped engaging post, said protruding post is provided thereover with a torsion spring, in order that said elastic pusher sheet is elastically pushed back to its original position;

said lower housing is provided with a battery chamber opening downwards to be covered with a battery lid, both ends of said battery chamber are provided therein with a plurality of polar sheets as electrodes, and is provided at the central area thereof with a plurality of screw holes for installation of an oscillating circuit, a plurality of protruding posts for fixedly mounting a heater fixing seat, a buzzer for mounting on an arciform protruding ring and an engaging hole for engaging a clamping member; said lower housing is further provided laterally with a switch hole for switching the modes of mosquito repelling/killing, and is provided with an electric power spigot for connecting outwardly to a power supply.

2. A portable mosquito repelling/killing device as in claim 1, wherein, said elastic pusher sheet is provided with a guide rod for sliding displacement of said elastic pusher sheet in a guide groove, said elastic pusher sheet is also provided with a plurality of gas emitting holes for emitting odor which kills mosquitoes.

3. A portable mosquito repelling/killing device as in claim 2, wherein, said guide rod has a hole thereon to receiving therein a torsion spring, said torsion spring renders said elastic pusher sheet elastic and able to move back automatically to its original position.

4. A portable mosquito repelling/killing device as in claim 1, wherein, said heater fixing seat is provided with a recess which is mounted therein with a spring, said spring is used to abut an electric heater against a copper sheet of positive polarity to uniformly distribute heat on said copper sheet.

5. A portable mosquito repelling/killing device as in claim 1, wherein, said protruding posts provided on said lower housing have springs thereon in corresponding number to that of said protruding posts, in order to push said heater fixing seat upwardly to abut against said mosquito-repellent slice of incense tightly to avoid dropping of said slice of incense.

6. A portable mosquito repelling/killing device as in claim 1, wherein, said oscillating circuit is provided with an LED power indicating light to display the state of said power supply.

\* \* \* \* \*